(12) United States Patent
Clapp et al.

(10) Patent No.: US 7,524,807 B2
(45) Date of Patent: Apr. 28, 2009

(54) RINSE-OFF PERSONAL CARE COMPOSITIONS COMPRISING ANIONIC AND/OR NONIONIC PERFUME POLYMERIC PARTICLES

(75) Inventors: Mannie Lee Clapp, Mason, OH (US); Robert Richard Dykstra, Cleves, OH (US); Rebecca Ann Taylor, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 749 days.

(21) Appl. No.: 10/698,871

(22) Filed: Oct. 31, 2003

(65) Prior Publication Data
US 2004/0092414 A1    May 13, 2004

Related U.S. Application Data

(60) Provisional application No. 60/423,005, filed on Nov. 1, 2002.

(51) Int. Cl.
*C11D 17/00* (2006.01)
(52) U.S. Cl. ...................................... 510/444
(58) Field of Classification Search ................ 510/444
See application file for complete search history.

(56) References Cited

U.S. PATENT DOCUMENTS

| | | | |
|---|---|---|---|
| 2,396,278 A | 3/1946 | Lind | |
| 2,438,091 A | 3/1948 | Lynch | |
| 2,486,921 A | 11/1949 | Byerly | |
| 2,486,922 A | 11/1949 | Strain | |
| 2,528,378 A | 10/1950 | McCabe et al. | |
| 2,658,072 A | 11/1953 | Kosmin et al. | |
| 3,577,518 A | 5/1971 | Shepherd et al. | |
| 3,929,678 A | 12/1975 | Laughlin et al. | |
| 3,946,749 A | 3/1976 | Papantoniou | |
| 3,958,581 A | 5/1976 | Abegg et al. | |
| 3,962,418 A | 6/1976 | Birkofer | |
| 4,741,855 A | 5/1988 | Grote et al. | |
| 5,573,709 A * | 11/1996 | Wells | 510/122 |
| 6,024,943 A | 2/2000 | Ness et al. | |
| 2001/0053803 A1 | 12/2001 | Kuwahara et al. | |

FOREIGN PATENT DOCUMENTS

| | | |
|---|---|---|
| EP | 0 925776 A2 | 6/1999 |
| WO | WO 97/48374 A2 | 12/1997 |
| WO | WO 98/28339 A1 | 7/1998 |
| WO | WO 98/28398 A1 | 7/1998 |
| WO | WO 99/09949 * | 3/1999 |
| WO | WO 00/41528 A1 | 7/2000 |
| WO | WO 01/62376 A2 | 8/2001 |

* cited by examiner

*Primary Examiner*—John R Hardee
(74) *Attorney, Agent, or Firm*—Bridget Murray; John M. Howell; Cynthia L. Clay

(57) ABSTRACT

Rinse-off personal care compositions comprising a perfume polymeric particle, which is useful as a delivery system for a perfume raw material ("PRM"), methods for making such personal care compositions and methods of treating substrates, such as skin and/or hair with such personal care compositions are provided.

19 Claims, No Drawings

US 7,524,807 B2

RINSE-OFF PERSONAL CARE COMPOSITIONS COMPRISING ANIONIC AND/OR NONIONIC PERFUME POLYMERIC PARTICLES

CROSS REFERENCE TO RELATED APPLICATION(S)

This application claims the benefit of U.S. Provisional Application No. 60/423,005, filed Nov. 1, 2002.

FIELD OF THE INVENTION

The present invention relates to rinse-off personal care compositions comprising a perfume polymeric particle, which is useful as a delivery system for a perfume raw material ("PRM"), methods for making such personal care compositions and methods of treating substrates, such as skin and/or hair with such personal care compositions.

BACKGROUND OF THE INVENTION

It is frequently desirable or advantageous to treat the surfaces of a variety of substrates, for example skin, with benefit agents such as perfumes, flavors, pharmaceuticals and/or biocontrol agents including biocides, insecticides, mildewcides, and the like. The objective of such treatment is generally to leave deposited on the surfaces of the substrates enough benefit agent so that there is a residual benefit imparted to the substrate surface.

In many consumer products, it is desirable for perfume, especially perfume raw materials to be released slowly over time. Since the most volatile perfume raw materials, referred to as "top notes" and "middle notes" are responsible for the "fresh feeling" consumers experience, it is desirable for the more volatile top notes to be released in a slow, controlled manner.

Since top notes are conventionally lost due to evaporation and/or dissolution in aqueous media, formulators have tried to minimize the loss of top and middle notes by exploring technologies that enhance the deposition of top notes and middle notes on substrates, even in the presence of water and/or even if the substrate subsequently is exposed to water and/or moisture.

Formulators have been less than successful in efficiently depositing top notes onto substrates. Prior art attempts include polymerizing the perfume, especially the perfume raw materials, into a polymeric particle. Other attempts have tried absorbing perfume into polymeric particles. These prior art attempts have failed to teach a polymeric particle that selectively absorbs/adsorbs top notes and middle notes, and especially top notes.

Accordingly, there is a need for a rinse-off personal care composition comprising a perfume polymeric particle that selectively absorbs/adsorbs PRM top and middle notes which enhance/increase the level of perfume raw materials that deposit onto and/or release from a substrate, a process for making such personal care compositions and methods for delivering PRM top notes to a substrate, particularly skin and/or hair.

SUMMARY OF THE INVENTION

The present invention fulfills the needs described above by providing personal care compositions comprising a perfume polymeric particle comprising perfume raw material (PRM) top notes and/or middle notes, processes for making such personal care compositions and methods for delivering PRM top notes and/or middle notes to human skin and/or hair of human and/or pet hair.

In one aspect of the present invention, a personal care composition comprising:
a) a perfume polymeric particle comprising:
   i) an anionic and/or nonionic polymer comprising an anionic and/or nonionic monomer; and
   ii) a perfume comprising one or more perfume raw material having a molecular weight of less than about 200 and/or a boiling point of less than about 250 C and/or a ClogP of less than about 3 and/or a Kovats Index value of less than about 1700; and
b) a personal care adjunct ingredient;

preferably, wherein more of the perfume raw material is deposited onto and/or released from a substrate when the perfume raw material is associated with the polymer in the form of the perfume polymeric particle than when the perfume raw material is not associated with the polymer in the form of the perfume polymeric particle as measured by the Perfume Deposition & Delivery Test Protocol I described herein, is provided.

In another aspect of the present invention, a personal care composition comprising an anionic and/or nonionic polymeric particle comprising an anionic and/or nonionic polymer including an anionic and/or nonionic monomer, wherein the anionic and/or nonionic polymer exhibits a greater affinity for a perfume raw material having a molecular weight of less than about 200 and/or a boiling point of less than about 250° C. and/or a ClogP of less than about 3 and/or a Kovats Index value of less than about 1700, than other perfume raw materials as measured by the Perfume Deposition & Delivery Test Protocol I and/or the Polymeric Particle Affinity Test Protocol II described herein; and a personal care adjunct ingredient; is provided.

In another aspect of the present invention, a personal care composition comprising an anionic or nonionic polymeric particle comprising an anionic or nonionic polymer including an anionic or nonionic monomer, wherein the anionic or nonionic polymer exhibits a greater affinity for a perfume raw material having a Kovats Index on DB-5 of less than about 1500 than other perfume raw materials having a Kovats Index on DB-5 of greater than about 1700 as measured by the Perfume Deposition & Delivery Test Protocol I and/or the Polymeric Particle Affinity Test Protocol II described herein; and a personal care adjunct ingredient; is provided.

In another aspect of the present invention, a personal care composition comprising an anionic or nonionic polymeric particle comprising an anionic or nonionic polymer including an anionic or nonionic monomer, wherein the anionic or nonionic polymer exhibits at least a 1.2× greater affinity for a perfume raw material having a Kovats Index on DB-5 of between about 1000 and 1500 than other perfume raw materials having a Kovats Index on DB-5 of greater than about 1700 as measured by the Perfume Deposition & Delivery Test Protocol I and/or the Polymeric Particle Affinity Test Protocol II described herein; and a personal care adjunct ingredient; is provided.

In still another aspect of the present invention, a method for making a personal care composition of the present invention, which exhibits enhanced fragrance intensity on skin and/or hair over time, comprising mixing an anionic or nonionic polymeric particle in accordance with the present invention with a perfume comprising a perfume raw material having a molecular weight of less than about 200 and/or a boiling point of less than about 250° C. and/or a ClogP of less than about 3 and/or a Kovats Index value of less than about 1700, is provided. The mixing step may occur before adding to a personal care adjunct ingredient and/or personal care formulation. Alternatively, the mixing step may occur in the presence of an adjunct ingredient and/or personal care formulation and/or the mixing may occur sequentially whereby the polymeric particle and perfume raw material may be present in an adjunct ingredient and/or personal care formulation prior to the other.

In yet another aspect of the present invention, a method for making a personal care composition according to the present invention comprises adding a perfume polymeric particle according to the present invention to a personal care adjunct ingredient, is provided.

In still even another aspect of the present invention, a method for treating human skin and/or human and/or pet hair in need of treatment comprising the step of contacting the human skin and/or human and/or pet hair with a perfume polymeric particle and/or a personal care composition of the present invention; and optionally, rinsing off the personal care composition such that the human skin and/or human and/or pet hair is treated, is provided.

In even yet another aspect of the present invention, a substrate treated by a method of the present invention is provided.

In still even yet another aspect of the present invention, a personal care composition comprising two or more perfume polymeric particles according to the present invention wherein the two or more perfume polymeric particles comprise at least one different monomer; and a personal care adjunct ingredient, is provided. By way of example, without being limited, one polymeric particle making up one of the perfume polymeric particles may be an anionic or nonionic polymeric particle and the other polymeric particle may be an anionic and/or nonionic and/or zwitterionic polymeric particle.

In one more aspect of the present invention, a personal care composition comprising two or more polymeric particles according to the present invention wherein the two or more polymeric particles comprise at least one different monomer; and a perfume comprising a perfume raw material having a molecular weight of less than about 200 and/or a boiling point of less than about 250° C. and/or a ClogP of less than about 3 and/or a Kovats Index value of less than about 1700; and a personal care adjunct ingredient, is provided. By way of example, without being limited, one polymeric particle may be an anionic or nonionic polymeric particle and the other polymeric particle may be an anionic and/or nonionic and/or zwitterionic polymeric particle.

In still one more aspect of the present invention, a personal care composition comprising a perfume polymeric particle according to the present invention; a polymeric particle according to the present invention; and a perfume comprising a perfume raw material having a molecular weight of less than about 200 and/or a boiling point of less than about 250° C. and/or a ClogP of less than about 3 and/or a Kovats Index value of less than about 1700, is provided.

Accordingly, the present invention provides a personal care composition comprising a perfume polymeric particle, a method for making a personal care composition and a method for treating human skin and/or human and/or pet hair with a perfume polymeric particle and/or a personal care composition.

One embodiment of the present invention relates to a perfume polymeric particle comprising: a polymer; and a perfume comprising a perfume raw material having one or more of the following characteristics: a molecular weight of less than about 200; a boiling point of less than about 250° C.; a ClogP of less than about 3; and a Kovats Index value of less than about 1700; wherein the Response factor (RF) of the perfume polymeric particle is at least about 1.6

Another embodiment of the present invention relates to a perfume polymeric particle comprising: a polymer and a perfume comprising more than one LKI perfume raw materials, each having a Kovats Index value of from about 1000 to about 1400, and the LKI perfume raw materials collectively provide a first Average Response Factor ($ARF_{LKI}$); and more than one HKI perfume raw materials, each having a Kovats Index value of greater than about 1700, and the HKI perfume raw materials collectively provide a second Average Response Factor ($ARF_{LKI}$); wherein the perfume polymeric particle exhibits a ratio of $ARF_{LKI}/ARF_{HKI}$ of at least about 1.2.

The present invention also relates to compositions comprising the perfume polymeric particles according to the above embodiments, and methods for making the perfume polymeric particles and the compositions containing them.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified.

All molecular weights as used herein are weight number molecular weights expressed as grams/mole, unless otherwise specified.

DETAILED DESCRIPTION OF THE INVENTION

Definitions:

"Non-polymerically associated" as used herein means that the perfume is absorbed in and/or adsorbed on and/or otherwise associated with the polymer after the polymer has been formed. In other words, the perfume is not present with the polymer during polymerization and/or melting of the polymer. Said another way, the perfume is mixed with preformed polymeric particles to produce a perfume polymeric particle in accordance with the present invention. For purposes of the present invention, this definition excludes encapsulation wherein a polymer encapsulates a perfume. Preferably the polymeric perfume particle is not a pre-formed perfume-loaded matrix system.

"Separate Addition" as used herein means that the perfume is absorbed in and/or adsorbed on and/or otherwise associated with the polymer only after the polymer or the perfume has been mixed with one or more adjunct ingredients that comprise the system-forming matrix. Said in another way, the perfume is mixed with preformed polymeric particles in the presence of adjunct ingredients or polymeric particles are mixed with perfume in the presence of adjunct ingredients to produce a perfume polymeric particle in the presence of a system-forming matrix. For purposes of the present invention, this definition of Separate Addition excludes encapsulation wherein a polymer encapsulates a perfume, although the polymer particle of the invention may include encapsulates that serve to encapsulate material that is not perfume raw material.

"Adjunct ingredients" as used herein means those ingredients that are used in the process for preparing the benefit agent polymeric delivery system. For example such a delivery system includes personal care/cleansing products, hair products and the like. Adjunct ingredients are also referred to as product formulation ingredients.

"Benefit agent delivery system" as used herein refers to a product composition comprising a benefit agent, a polymeric particle and optionally, an adjunct ingredient, combined in such a manner as to enhance or increase the deposition of benefit agent onto a substrate and/or the release of benefit agent from a substrate at any time point after said substrate has been exposed to said benefit agent delivery system. Benefit agent delivery systems include, but are not limited to, personal care/cleansing products.

As used herein, "directly applied", "direct applications" or "delivering directly" means that a benefit agent is applied to a substrate via the benefit agent delivery system such that the benefit provided by the benefit agent is realized and/or recognized prior to or without subsequent dilution. That is, this type of benefit delivery system can be formulated as a leave-on product, which is applied to the substrate without dilution or rinse off. For example, a benefit agent is sprayed onto a substrate and/or wiped on to a substrate, rather than having the benefit agent contact or deposit indirectly onto a substrate from a dilute solution (i.e., wash liquor). Nonlimiting examples include fine fragrance perfume applications or products beauty care products, such as creams, lotions, deodorants, antiperspirants, and other topical compositions; hair care products, such as hair spray, leave-in conditioners, and the like.

As used herein, "indirectly applied", "indirect applications" or "applied indirectly" means that the substrate is contacted with a dilute solution of the benefit agent delivery system, such as in an aqueous solution or dispersion of such a benefit agent delivery system. For purposes of this invention, a "dilute solution" of the delivery system is a solution that contains a concentration of the benefit agent that is at least about 10%, preferably at least about 30%, more preferably at least about 50% lower than the concentration of the benefit agent in the delivery system prior to such dilution. Such dilute solutions or dispersions can be formed by diluting the delivery system or the end product containing it with water. Nonlimiting example is bar soaps.

For purposes of this invention, an aqueous solution or dispersion of a delivery system is one which contains no more than about 5000 ppm, preferably no more than about 500 ppm, even more preferably no more than about 50 ppm, and most preferably no more than about 10 ppm and even sometimes no more than about 1 ppm, of the benefit agent.

Perfume

Perfumes comprise perfume raw materials ("PRMs"). PRMs can be characterized by their boiling point (B.P.) and/or their octanol/water partitioning coefficient (P), otherwise known as logP and when calculated, known as ClogP and/or molecular weight and/or Kovats index. The octanol/water partitioning coefficient of a PRM is the ratio between its equilibrium concentrations in octanol and in water. Since the partitioning coefficients of the perfume ingredients of this invention have high values, they are more conveniently given in the form of their logarithm to the base 10, logP. Thus the perfume ingredients of this invention have logP of less than about 3. The personal care compositions of the present invention preferably comprise at least 0.1% of one or more perfume raw materials.

The boiling points of many perfume ingredients are given in, e.g., "Perfume and Flavor Chemicals (Aroma Chemicals)," Steffen Arctander, published by the author, 1969, incorporated herein by reference.

The logP of many perfume ingredients has been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume ingredients which are useful in the present invention.

In addition to ClogP values, KI values (Kovats Index) may be used to identify perfume raw materials. The Kovats Retention Index system is an accurate method for reporting gas chromatographic data for interlaboratory substance identification. It is used for eliminating the effects of instrument parameters on retention correlations in peak identification by GC. The Kovats Index value of many perfume ingredients has been reported, or can be calculated from the following equation.

$$I = 100[n + (N - n)\frac{\log t'_r(\text{unknown}) - \log t'_r(n)}{\log t'_r(N) - \log t'_r(n)}]$$

where n is the number of carbon atoms in the smaller alkene; N is the number of carbon atoms in the larger alkene; $t'_r(n)$ is the adjusted retention time of the smaller alkene; and $t'_r(N)$ is the adjusted retention time of the larger alkene. It is noted that this equation applies to a particular stationary phase in the GC column. Based on the above equation, the Kovats Index for a linear alkane equal to 100 times the number of carbon atoms. For example, octane has a KI value of 800, and decane would have a KI value of 1000. In another example, octanol has a KI value of 826, on a particular phase and hexadecanol would have a KI value of 1626. The KI value used herein are determined using polydimethylsiloxane as the non-polar stationary phase in the column (referred to as a "DB-5 column").

This definition makes the Kovats Index (KI) or (RI) for a linear alkane equal to 100 times the number of carbon atoms. For octane I=800, and for decane I=1000. Octanol may be 826 for example on a particular phase and extrapolated to hexadecanol the KI would be 1626.

The perfume associated with the polymeric particle of the present invention comprises PRMs having a molecular weight of less than about 200 and/or a boiling point less than about 250° C. (measured at the normal, standard pressure) and/or a ClogP of less than about 3, and/or a Kovats Index value of less than about 1700. Such PRMs are often referred to as "top notes".

The perfume composition as used in the present invention will preferably comprise at least about 25 weight percent of top and middle notes, more preferably at least about 50 weight percent of top and middle notes, and even more preferably at least 75 weight percent of top and middle notes, wherein top and middle notes are those PRMs with a Kovats Index value of less than about 1700.

The perfume composition as used in the present invention will more preferably comprise at least about 25 weight percent of top notes, more preferably at least about 50 weight percent of top notes, and even more preferably at least 75 weight percent of top notes, wherein top notes are those PRMs with a Kovats Index value of less than about 1400.

Nonlimiting examples of suitable PRMs having a molecular weight of less than about 200 and/or a boiling point of less than about 250° C. and/or a ClogP of less than about 3 include, but are not limited to, benzaldehyde, benzyl acetate, laevo-carvone, geraniol, hydroxycitronellal, cis-jasmone, linalool, nerol, phenyl ethyl alcohol, alpha-terpineol, eugenol, indole, methyl cinnamate, methyl-N-methyl anthranilate, vanillin, iso-bornyl acetate, carvacrol, alpha-citronellol, citronellol, anisic aldehyde, linalyl acetate, methyl anthranilate, flor acetate and dihydro myrcenol.

In one embodiment, the PRMs having a molecular weight of less than about 200 and/or a boiling point of less than about 250° C. and/or a ClogP of less than about 3 are selected from the group consisting of: benzaldehyde, benzyl acetate, laevo-carvone, geraniol, hydroxycitronellal, cis-jasmone, linalool, nerol, phenyl ethyl alcohol, alpha-terpineol, dihydro myrcenol, citronellol, anisic aldehyde, linalyl acetate, methyl anthranilate, flor acetate and mixtures thereof.

Additional PRMs suitable for use in the personal care compositions of the present invention are identified in the KI Table described below.

Representative PRMs are identified in the KI Table described herein.

| PRM | KI Value | CAS # | MW |
|---|---|---|---|
| Very Low KI (VLKI) | | | |
| ethyl acetate | 604 | 141-78-6 | 88.1 |
| methyl-2-methylpropanoate | 685 | 547-63-7 | 102.1 |
| 3-hydroxy-2-butanone | 718 | 513-86-0 | 88.1 |
| 1-hexen-3-ol | 789 | 4798-44-1 | 100.1 |
| propyl propanoate | 812 | 106-36-5 | 116.1 |
| ethyl 2-me butyrate | 849 | 7452-79-1 | 130.1 |
| (Z)-3-hexen-1-ol | 858 | 928-96-1 | 100.1 |
| propyl butyrate | 898 | 105-66-8 | 130.1 |
| alpha-Pinene | 937 | 80-56-8 | 136.1 |
| Low KI (LKI) | | | |
| beta-Pinene | 1002 | 127-91-3 | 136.1 |
| Limonene | 1033 | 138-86-3 | 136.1 |
| benzyl alcohol | 1037 | 100-51-6 | 108.1 |
| Melonal | 1055 | 106-72-9 | 140.1 |
| dihydromyrcenol | 1072 | 18479-58-8 | 156.2 |
| methyl benzoate | 1081 | 93-58-3 | 136.1 |
| Linalool | 1100 | 78-70-6 | 154.1 |
| Ligustral | 1090, 1119 | 68039-49-6 | 138.1 |
| methyl cinnamate | 1113 | 103-26-4 | 162.1 |
| phenyl ethyl alcohol | 1122 | 60-12-8 | 122.1 |
| Citronellal | 1155 | 106-23-0 | 154.1 |
| benzyl acetate | 1164 | 140-11-4 | 150.1 |
| l-carvone | 1227 | 6485-40-1 | 150.1 |
| Citronellol | 1237 | 106-22-9 | 156.2 |
| Citral | 1254 | 5392-40-5 | 152.1 |
| anisic aldehyde | 1271 | 123-11-5 | 136.2 |
| Geraniol | 1275 | 106-24-1 | 154.1 |
| ethyl benzoate | 1300 | 93-89-0 | 150.1 |
| methyl anthranilate | 1359 | 134-20-3 | 151.2 |
| Eugenol | 1364 | 97-53-0 | 164.1 |
| beta damascenone | 1386 | 23726-93-4 | 190.1 |
| delta-damascone | 1394 | 71048-82-3 | 192.2 |
| Medium KI (MKI) | | | |
| Vanillin | 1410 | 121-33-5 | 152.0 |
| alpha-ionone | 1425 | 127-41-3 | 192.2 |
| flor acetate | 1443 | 2500-83-6 | 192 |
| Gamma ionone | 1445 | 79-76-5 | 192.2 |
| Geranyl propionate | 1476 | 105-91-9 | 210.2 |
| beta-ionone | 1493 | 14901-07-6 | 192.2 |
| sandalore | 1512 | 065113-99-7 | 210.2 |
| Geranyl acetate | 1577 | 105-87-3 | 196.1 |
| helional | 1589 | 1205-17-0 | 192.1 |
| High KI (HKI) | | | |
| methyl-(E)-cinnamate | 1700 | 1754-62-7 | 162.1 |
| Iso E Super | 1703 | 54464-57-2 | 234.2 |
| hexyl salicylate | 1713 | 6259-76-3 | 222.1 |
| delta dodecalactone | 1713 | 713-95-1 | 198.2 |
| nonanoic acid | 1762 | 112-05-0 | 158.1 |
| hexyl cinnamic aldehyde | 1770 | 101-86-0 | 216.2 |
| benzyl benzoate | 1791 | 120-51-4 | 212.1 |
| cedryl acetate | 1811 | 77-54-3 | 264.2 |
| Ambrox | 1812 | 100679-85-4 | 236.2 |
| exaltolide | 1876 | 106-02-5 | 240.2 |
| phenyl ethyl benzoate | 1887 | 94-47-3 | 226.2 |
| galaxolide | 1893 | 1222-05-5 | 258.2 |
| exaltenone | 1901 | 14595-54-1 | 222.2 |
| isoeugenol | 1902 | 97-54-1 | 164.1 |
| benzyl salicylate | 1904 | 118-58-1 | 228.1 |
| phenyl ethyl phenyl acetate | 1945 | 102-20-5 | 240.1 |
| musk C14/Zenolide | 1959 | 54982-83-1 | 256.2 |
| geranyl benzoate | 1985 | 100012-96-0 | 258.2 |
| phenyl ethyl salicylate | 1987 | 87-22-9 | 242.1 |
| (E,E)-farnesol | 2002 | 106-28-5 | 222.2 |
| ethylene brassylate | 2060 | 105-95-3 | 270.2 |
| tetradecanol | 2116 | 4706-81-4 | 214.2 |
| Phytol | 2128 | 7541-49-3 | 296.5 |
| acetovanillone | 2292 | 498-02-2 | 166.1 |

For the purpose of this invention and the test protocols described herein, low KI PRMs ("top notes") refer to PRMs having Kovats Index value less than about 1400, and high KI PRMs ("base notes") refer to PRMs having Kovats Index value greater than about 1700, and medium KI PRMs ("middle notes") refer to PRMs having Kovats Index value between about 1400 and about 1700.

Protocol I Perfume Deposition & Delivery Test

The perfume polymeric particles useful in the perfume compositions of the present invention encompass perfume polymeric particles that enhance/increase the level of perfume raw materials that deposit onto and/or release from a substrate.

For purposes of determining if the perfume polymeric particles enhance/increase deposition onto and/or release from a substrate, the following test protocols are provided. A fabric article in an aqueous medium is used as the substrate for purposes of these test protocols. The Perfume Deposition & Delivery Test can be used to determine if a perfume polymeric particle falls within the scope of the present invention. A perfume polymeric particle falls outside the scope of the present invention when all of the following test protocols indicate so.

Protocol IA (Perfume Raw Material Delivery or Longevity Test I):

Each benefit agent delivery system that comprises a perfume raw material and a polymeric particle is tested in accordance with Protocol IA. Each perfume raw material (PRM) commonly found in a perfume is tested with each polymeric particle (PP) to determine if the combination (PRM-PP) demonstrates an enhancement and/or increase in the level of PRM delivered and/or a longevity that is greater than that obtained for the PRM alone.

Multiple PRMs may be tested together, at the same time, in the presence of single or multiple polymeric particles (PPs), as long as the analytical measurements (such as chromatography) are not compromised by such combination.

For example, a PRM delivery system that contains three PRMs, and a single polymeric particle ($PP^1$) requires the following single-variable test: the Sample, which contains $PRM^1$-$PP^1$, $PRM^2$-$PP^1$ and $PRM^3$-$PP^1$, is compared with the Control, which contains $PRM^1$, $PRM^2$ and $PRM^3$, provided that said PRMs are chromatographically separable such that the amount of each PRM can be determined in the presence of the other. Perfume raw materials that are not chromatographically separable from one another must be run in separate tests.

In another example where $PRM^1$ and $PRM^3$ are not separable, then one of the following tests is required:

I. sample ($PRM^1$-$PP^1$ and $PRM^2$-$PP^1$) vs. control ($PRM^1$ and $PRM^2$), and sample ($PRM^3$-$PP^1$) vs. control ($PRM^3$); or II. sample ($PRM^2$-$PP^1$ and $PRM^3$-$PP^1$) vs. control ($PRM^2$ and $PRM^3$), and sample ($PRM^1$-$PP^1$) vs. control ($PRM^1$); or III. sample ($PRM^1$-$PP^1$) vs. control ($PRM^1$), sample ($PRM^2$-$PP^1$) vs. control ($PRM^2$), and sample ($PRM^3$-$PP^1$) vs. control ($PRM^3$).

The PRM in any test should not be present at a concentration much greater than the concentration of another PRM in the same test such that the results are affected (i.e., causing the results to be significantly different than when the PRMs are tested separately). Typically, when the concentrations of the PRMs are within a factor of 10, the results do not appear to be affected by the presence of other PRMs in the same test. If test results appear to be affected, separate tests for the PRMs are required.

(a) Sample Concentration

The concentrations of PRMs and PP to be used in the Longevity Test (LT) are the lowest concentrations, in a series of solutions based on $TS_0$, at which each PRM in the test solution is detected in the headspace sample collected from the treated substrate at one or more of the designated time points. If this condition is not met by $TS_0$, the concentrations of PRMs and PP in the test solution are doubled and the new solution ($TS_1$) is tested in the same manner. The process is repeated until the above PRM detection condition is met. The concentrations of PRMs and PP in the test solution ($TS_n$) that meets the above PRM detection condition relate to the concentrations of the PRMs and PP in $TS_0$ according to the following equation:

$$[PRM, PP] \text{ in } TS_n = 2^n [PRM, PP] \text{ in } TS_0; \text{ where } n=0, 1, 2, 3 \ldots$$

In some instances, the process of doubling the concentration is repeated until the concentration of the PRMs and of PP both exceed 5% by weight of the test solution and the above PRM detection condition is still not met. Then, the following alternatives may be used in conducting the test. The aliquot of $TS_n$ transferred onto the substrate is increased from 1.0 mL to 3 mL, then to 10 mL, until (i) the above PRM detection condition is met, or (ii) with respect to individual PRM that has a concentration greater than 0.1 wt % of the perfume, at least one of the following two alternative conditions is met:

(1) at least 80% of the low KI PRMs in the test solution and at least 80% of high KI PRMs in the test solution are detected in the headspace sample collected from the treated substrate at one or more of the designated time points; or (2) at least 10 of the low KI PRMs in the test solution and at least 5 of the high KI PRMs in the test solution are detected in the headspace sample collected from the treated substrate at one or more of the designated time points.

b) The Test Procedure

The test solution is prepared by dissolving or mixing PRM(s) and PP(s) that are to be tested together into a composition at concentrations equal to those used in a consumer product. For example, the respective concentration of PRM(s) and PP(s) in a consumer product may be 2.0% and 4.0%. The solution is closed to the atmosphere and aged for 24 hours at room temperature to obtain the initial test solution, designated $TS_0$.

A 4 cm diameter fabric circle, weighing 0.45 to 0.65 g, is cut from an 86/14 cotton/poly terry wash cloth (obtained from EMC, 7616 Reinfold Drive, Cincinnati, Ohio 45237) and used as the test substrate. The weights of substrates in a given test should be within ±0.02 g of one another. A 1.0 mL aliquot of $TS_0$ is transferred by a pipette onto the substrate, with the pipette pointing close to the center of the substrate. Then, a 1.0 mL aliquot of deionized (DI) water is added to the substrate in the same manner. The substrate is lathered by rubbing against the palm of a nitrile-gloved hand for 1 minute. The substrate is then placed in a bottle containing 40 mL of 35° C. DI water; the bottle is capped and shaken for 30 seconds. The substrate is then removed using forceps and gently blotted on paper towels to remove excess water. The substrate, treated by the above steps (including charging with test solution, diluting, lathering/washing and rinsing) is left open to the atmosphere under ambient conditions to air dry for the specified period of time. Subsequently, the substrate is analyzed via headspace gas chromatography (HSGC) to determine the amount of each perfume raw material in the headspace at each of the following times: 2, 6 and 24 hours. Perfume is analyzed by gas chromatography—mass spectrometry (GC-MS).

c) Headspace Gas Chromatography (HSGC)

A suitable equipment is described by S. Maeno and P. A. Rodriguez in J. Chromatography, vol. A731 (1996) pages 201-215. The equipment includes:

1) a headspace collector to contain the substrate (treated and air dried as described above) and allow PRM(s) to partition into the headspace and reach equilibrium;

2) a trap containing a porous polymer, which has the ability to retain aroma materials;

3) a transfer device to transfer the trapped headspace vapors onto a GC for quantitative analysis; and 4) GC-MS with headspace detection capabilities, and uses helium as the mobile phase.

A substrate, which has been treated and air dried for a specified time period as described above, is placed in a headspace collector and allowed to partition and reach equilibrium, which takes about two hours. After equilibration, a trap containing a porous polymer having the ability to retain aroma materials, preferably Tenax® TA 35/60 mesh (available from Gerstel, Inc., Baltimore, Md.), is operatively connected to the headspace collector to capture the equilibrated headspace vapors. A transfer device is used to transfer the trapped headspace vapors, which contains perfume raw materials, onto a GC for quantitative analysis. This device is able to heat the porous polymer trap containing the collected headspace vapors, and transfer the vapors to a cold trap cooled to lower than about −100° C. (generally by liquid nitrogen). Following complete transfer to the cold trap, the cold trap is flash heated in a short period of time, typically about 1 minute, to a temperature of about 280° C., resulting in the transfer of the headspace vapors directly onto a capillary GC column.

A typical column is a 30-60 meters long with an inner diameter of 0.18-0.32 mm, with a stationary phase (for example, 100% dimethylpolysiloxane or phenylmethylpolysiloxane containing about 5% phenyl). The GC-MS has the capability of identifying and quantifying PRMs of the aldehyde- or ketone-type. Identification is accomplished via Mass Spectrometry and quantification is performed using a separate detector, such as an FID (flame ionization) detector or PID (photo ionization) detector. Specific GC/MS conditions are described below.

The perfume components are separated on a DB-5 column (dimethylsiloxane, 60 m×0.32 mm, 0.25 μm) in split mode to both an MS (for identification) and FID (for quantitation). GC conditions are as following: the sample is held at oven temperature of about 35° C. for 2 min, then the GC is programmed to ramp up to 200° C. at 4° C./min, followed by a ramp to 325° C. at 10° C./min. Inlet pressure was kept constant at 13.7 psi (9.45 N/m$^2$), which is equivalent to an inert gas (e.g., helium) flow of about 2.4 mL/min. MS conditions are as following: scan range 35 to 400 amu (atomic units). Transfer line is maintained at about 250° C.

The quantitative measurements should be reproducible to within 20% of the average from the runs. If the result from a given run is not within said range, the data from said run should be discarded and the test repeated. The average of at least 3 satisfactory runs is reported.

d) Exemplary Results

A given test solution $TS_n$ meeting the above PRM detection condition or the alternative condition(s) is prepared. A second test solution $TS_c$ is prepared containing all the components of $TS_n$ at the same concentrations as in $TS_n$ except that the polymeric particles are not included. Identical procedure is carried out using a solution ($TS_c$) containing no polymeric particles (PPs).

The solution $TS_c$ serves as the control solution in the test. Data are gathered at identical test conditions for a given set of test solution ($TS_c$ and $TS_n$) as described above and analyzed via headspace gas chromatography (HSGC) to determine the amount of each PRM in the headspace at each of the following three designated times: 2, 6 and 24 hours. The following tables demonstrate the type of results that can be obtained from a Longevity Test I.

| Longevity Test (Time = 24 h): |||||| 
|---|---|---|---|---|---|
| HSGC Area Count for PRM having Low KI* (LKI) value with and without PP$^1$ |||||| 
| PRM$^1$ || PRM$^2$ || PRM$^3$ || 
| $TS_c$ | $TS_n$ | $TS_c$ | $TS_n$ | $TS_c$ | $TS_n$ |
| 38,000 | 418,000 | 250,000 | 250,000 | 55,000 | 275,000 |
| RF = 11x || RF = 1.0x || RF = 4.1x ||
| ARF$_{LKI}$ value = Average Response Factor value ($TS_n/TS_c$) = 5.4 |||||| 
| HSGC Area Count for PRM having High KI* (HKI) value with and without PP$^1$ |||||| 
| PRM$^4$ || PRM$^5$ || PRM$^6$ || 
| $TS_c$ | $TS_n$ | $TS_c$ | $TS_n$ | $TS_c$ | $TS_n$ |
| 110,000 | 143,000 | 10,000 | 12,000 | 550,000 | 550,000 |
| RF = 1.3x || RF = 1.2x || RF = 1.0x ||
| ARF$_{HKI}$ value = Average Response Factor value ($TS_n/TS_c$) = 1.2 |||||| wherein RF means Response Factor, which is the ratio of the amount of benefit agent (e.g., perfume raw material) in the headspace collected from $TS_n$ sample at a specific time point compared to the amount of the same benefit agent in the headspace collected from $TS_c$ at the same time point; ARF value is the Average Response Factor value, which is the mean of the RFs from all measured PRMs in the test solution.

A Longevity Benefit of a perfume polymeric particle is confirmed for a particular PRM when, at any one of the three designated times points, the RF of the particular PRM is at least about 1.2, preferably at least about 1.6, more preferably at least about 2, even more preferably at least about 3, still more preferably at least about 5, and still even more preferably at least about 10. If the longevity benefit is confirmed, then the perfume polymeric particle falls within the scope of the present invention.

For example, the data in the above tables confirm a longevity benefit for PRM$^1$ and PRM$^3$ in the presence of PP$^1$, because at air drying time equals to 24 hours, both PRM/PP exhibit a greater HSGC area count from $TS_n$ than that of $TS_c$.

Additionally, a perfume polymeric particle falls within the scope of the present invention if the longevity benefit is confirmed for the PRM mixture. The longevity benefit is confirmed for a PRM mixture when, at any one of the three designated time points, the RFs or ARF meet one or more of the following requirements:

1. When the Response Factor observed for one or more LKI (top notes) perfume raw material is greater than the Response Factor observed for any HKI perfume raw material; or 2. When the Response Factor observed for one or more LKI perfume raw material is greater than the average Response Factor observed for HKI perfume raw materials; or 3. When the Average Response Factor (ARF) observed for all measured Low Kovats Index (LKI) perfume raw materials (PRMs) is greater than the ARF observed for all measured High Kovats Index (HKI) perfume raw materials (PRMs).

For example, the data in the above tables confirm a longevity benefit for perfume polymeric particles of a PRM mixture (containing PRM$^{1-6}$) and PP$^1$.

4. When the Average Response Factor (ARF) observed for all measured LKI PRMs is at least about 1.2, preferably at least about 1.6, more preferably at least about 2, even more preferably at least about 3, still more preferably at least about 5, and still even more preferably at least about 10 greater than the ARF observed for all measured HKI PRMs. Specifically, the ratio of ARF$_{LKI}$ value/ARF$_{HKI}$ value also called the selectivity ratio is at least about 1.2, preferably at least about 1.6, preferably at least about 2, more preferably at least about 3, even more preferably at least about 5, still even more preferably at least about 10. Moreover and without wishing to be bound by theory, this selectivity ratio also demonstrates a selectivity or affinity of the polymeric particles for low KI PRMs than high KI PRMs.

Protocol IB (Perfume Accord Delivery or Longevity Test II):

Each benefit agent delivery system that comprises a polymeric particle is tested in accordance with Protocol IB, in which an accord of perfume raw materials are to be tested with each polymer particle (PP) to determine if the combination of PRMs and PP(s) demonstrates an enhancement or increase in the level of PRM(s) delivered to or released from a substrate, or a sustained release time, compared to that obtained for the PRM alone.

Under Protocol IB, total of 20 PRMs (including 10 PRMs having a Kovats Index value between 1000 and 1400 and 10 PRMs having a Kovats Index value greater than 1700, all of which are selected from the representative PRMs table herein above) must be evaluated in the perfume polymeric particles as described in the above Longevity Test for $TS_n$ and $TS_c$ with the following changes.

The relative concentration of each PRM in the mixture of 20 PRMs to be used in the Longevity Test is the concentration at which at least 18 of the 20 PRMs in the test solution is detected by HSGC in at least one of the designated time points (2, 6 or 24 hours). If this condition is not met by $TS_0$, the overall concentration of the PRM in the test solution is doubled and the new solution ($TS_1$) is tested in the same manner. The process is repeated until the condition is met, provided that the overall concentration of the PRMs in the test solution shall not exceed 5%. Should less than 18 of the 20 PRMs in the TS be detected by HSGC in at least one of the designated time points, the relative concentrations of the 20 PRMs should be adjusted by increasing the concentrations of PRMs not detected by HSGC. Should the condition still not be met for the benefit agent delivery system being evaluated, the PRM(s) not detected should be replaced by alternative PRM(s) selection from the representative table herein above.

In addition, if the HSGC area count for $TS_n$ is less than the HSGC area count for $TS_c$ for any of the 20 PRMs, the Response Factor value for such PRM(s) shall be defined as 1.0x.

In addition, if the HSGC area count for a low Kovats Index PRM in $TS_c$ is zero, e.g., its. HSGC area count is below the instruments detection limit, and the HSGC area count for the same low Kovats Index PRM in $TS_n$ is nonzero, then new test solution should be prepared, as described above, to increase the PRM level in both $TS_n$ and $TS_c$, so as to obtain non-zero values of the HSGC area counts. Should such steps not provide a nonzero value for the PRM in $TS_c$, the Response Factor value for such PRM(s) shall be defined as 10x.

Similarly, should the HSGC area count for high Kovats Index PRM in $TS_n$ be zero, e.g., its HSGC area count being below the instruments detection limit, and should the HSGC area count for high Kovats Index PRM in $TS_c$ be non-zero, then steps should be taken, as described above, to increase the PRM level in both $TS_n$ and $TS_c$, so as to obtain non-zero values. Should such steps not provide a nonzero value for the PRM in $TS_n$ the PRM shall be replaces by an alternate PRM in the table such that non-negative values is obtained for the Response Factor in both $TS_n$ and $TS_c$.

The following table demonstrates the type of results that can be obtained from a Longevity Test II.

| Longevity Test (Time = 24 h): HSGC Area Count for PRM having Low KI value with and without $PP^1$ | | | | | |
|---|---|---|---|---|---|
| $PRM^1$ | | $PRM^2$ | | $PRM^3$ | |
| $TS_c$ | $TS_n$ | $TS_c$ | $TS_n$ | $TS_c$ | $TS_n$ |
| ND | 418,000 | 250,000 | 250,000 | 55,000 | 275,000 |
| RF = $TS_n/TS_c$ = 10x | | RF = $TS_n/TS_c$ = 1.0x | | RF = $TS_n/TS_c$ = 4.1x | |
| $ARF_{LKI}$ value = Average Response Factor value ($TS_n,TS_c$) = 5.0 | | | | | |

ND = Not detected.

Polymeric particles fall within the scope of the present invention when the ARF observed for 10 of the Low Kovats Index (LKI) PRMs is greater than the ARF observed for 10 of the High Kovats Index (HKI) PRMs. Specifically, the ratio of $ARF_{LKI}$ value/$ARF_{HKI}$ value also called the selectivity ratio is at least about 1.2, preferably at least about 1.6, preferably at least about 2, more preferably at least about 3, even more preferably at least about 5, still even more preferably at least about 10. Moreover, this selectivity ratio also demonstrates a selectivity or affinity of the polymeric particles for low KI PRMs than high KI PRMs.

Polymeric Particle Affinity Test

The polymeric particles useful in the personal care compositions of the present invention encompass anionic or nonionic polymeric particles comprising an anionic or nonionic polymer that exhibits a greater affinity for a perfume raw material having a molecular weight of less than about 200 and/or a boiling point of less than about 250° C. and/or a ClogP of less than about 3 and/or a Kovats Index value of less than about 1700 than other perfume raw materials. To determine if an anionic or nonionic polymeric particle falls within the scope of the present invention, the following Polymeric Particle Affinity Test Protocol II has been provided.

Polymeric Particle Affinity Test Protocol II

An aqueous dispersion of the polymeric particles is thoroughly mixed with perfume oil and then separated via ultra centrifugation for 16 hours at 40,000 rpm. Subsequent to centrifugation, the contents separate into distinguishable layers, e.g. perfume oil (top), aqueous layer (middle), and particle layer (bottom). A sample from each layer is extracted with a suitable organic solvent (e.g. acetone) and analyzed via GC/MS for perfume identification using the instrument conditions given above. A polymeric particle material that exhibits the properties of the present invention will show selectivity toward perfume raw materials contained in the particle layer having a molecular weight of less than about 200 and/or a boiling point of less than about 250° C. and/or a ClogP of less than about 3 and/or a Kovats Index value of less than about 1700.

Anionic or Nonionic Polymeric Particle (PP)

The anionic or nonionic polymer particles are polymerized from at least one anionic or nonionic monomer and optionally, one or more cationic monomers, preferably also a crosslinking monomer. The polymerization process may be any suitable process known in the art, such as emulsion and/or suspension and/or miniemulsion polymerization. During the polymerization, an emulsifier and/or stabilizer may be present to keep the polymeric particles from coagulating and/or crashing out of the aqueous solution in which the polymeric particles are being formed.

Perfume Polymeric Particles are defined as charged (anionic or cationic) if they have a non-zero zeta potential as defined below. Zeta potentials are determined by using a Brookhaven Zeta Plus Zeta potential analyzer. A dilute suspension of Perfume Polymeric Particles (i.e. 0.1 g particles in 25 g deionized (DI) water, or 1 drop of PPP if they are supplied as a solution) is first prepared, then 1 to 2 drops of this suspension is diluted in 10 mM KCl. The pH of the system is not adjusted. Zeta potential analysis is performed on the sample diluted in KCl. For the purposes of this invention, particles are defined as anionic if the mean of 10 runs results in a negative zeta potential, and cationic if the mean results in a positive zeta potential. The monomers of the polymeric particle may be selected such that the resulting anionic or nonionic polymeric particle has an affinity for perfume raw materials having a molecular weight of less than about 200, a boiling point of less than about 250° C. and a ClogP of less than about 3 and/or a Kovats Index value of less than about 1700.

In another embodiment, the monomers of the polymeric particle may be selected such that the resulting anionic or nonionic polymeric particle exhibits a greater affinity for a perfume raw material having a Kovats Index on DB-5 of between about 800 and 1500 than other perfume raw materials having a Kovats Index on DB-5 of greater than about 1700 as measured by the Perfume Deposition & Delivery Test Protocol I and/or the Polymeric Particle Affinity Test Protocol II described herein.

In yet another embodiment, the monomers of the polymeric particle may be selected such that the resulting anionic or nonionic polymeric particle exhibits a greater affinity for a perfume raw material having a Kovats Index on DB-5 of between about 1000 and 1500 than other perfume raw materials having a Kovats Index on DB-5 of greater than about 1700 as measured by the Perfume Deposition & Delivery Test Protocol I and/or the Polymeric Particle Affinity Test Protocol II described herein.

In still yet another embodiment, the monomers of the polymeric particle may be selected such that the resulting anionic or nonionic polymeric particle exhibits selectivity ratio of 1.2× affinity for at least four perfume raw materials having a Kovats Index on DB-5 of between about 1000 and 1400 than for at least four perfume raw materials having a Kovats Index on DB-5 of greater than about 1600 as measured by the Perfume Deposition & Delivery Test Protocol I described herein.

In still another embodiment, the monomers of the polymeric particle may be selected such that the resulting anionic or nonionic polymeric particle exhibits selectivity ratio of 1.2× affinity for a perfume raw material having a Kovats Index on DB-5 of between about 1000 and 1500 than other perfume raw materials having a Kovats Index on DB-5 of greater than about 1700 as measured by the Perfume Deposition & Delivery Test Protocol I and/or the Polymeric Particle Affinity Test Protocol II described herein.

In even another embodiment, the monomers of the polymeric particle may be selected such that the resulting anionic or nonionic polymeric particle exhibits selectivity ratio of 1.2× affinity for a perfume raw material having a Kovats Index on DB-5 of between about 1000 and 1400 than other perfume raw materials having a Kovats Index on DB-5 of greater than about 1700 as measured by the Perfume Deposition & Delivery Test Protocol I and/or II described herein.

In still yet another embodiment, the monomers of the polymeric particle may be selected such that the resulting anionic or nonionic polymeric particle exhibits selectivity ratio of 1.6× affinity for at least four perfume raw materials having a Kovats Index on DB-5 of between about 1000 and 1400 than for at least four perfume raw materials having a Kovats Index on DB-5 of greater than about 1600 as measured by the Perfume Deposition & Delivery Test Protocol I described herein.

In still another embodiment, the monomers of the polymeric particle may be selected such that the resulting anionic or nonionic polymeric particle exhibits selectivity ratio of 1.6× affinity for a perfume raw material having a Kovats Index on DB-5 of between about 1000 and 1500 than other perfume raw materials having a Kovats Index on DB-5 of greater than about 1700 as measured by the Perfume Deposition & Delivery Test Protocol I and/or the Polymeric Particle Affinity Test Protocol II described herein.

In even another embodiment, the monomers of the polymeric particle may be selected such that the resulting anionic or nonionic polymeric particle exhibits selectivity ratio of 1.6× affinity for a perfume raw material having a Kovats Index on DB-5 of between about 1000 and 1400 than other perfume raw materials having a Kovats Index on DB-5 of greater than about 1700 as measured by the Perfume Deposition & Delivery Test Protocol I and/or II described herein.

In even another embodiment, the monomers of the polymeric particle may be selected such that the resulting anionic or nonionic polymeric particle exhibits selectivity ratio of 2× affinity for a perfume raw material having a Kovats Index on DB-5 of between about 1000 and 1400 than other perfume raw materials having a Kovats Index on DB-5 of greater than about 1700 as measured by the Perfume Deposition & Delivery Test Protocol I and/or II described herein.

In still another embodiment, the monomers of the polymeric particle may be selected such that the resulting anionic or nonionic polymeric particle exhibits selectivity ratio of 2× affinity for a perfume raw material having a Kovats Index on DB-5 of between about 1000 and 1500 than other perfume raw materials having a Kovats Index on DB-5 of greater than about 1700 as measured by the Perfume Deposition & Delivery Test Protocol I and/or the Polymeric Particle Affinity Test Protocol II described herein.

In still yet another embodiment, the monomers of the polymeric particle may be selected such that the resulting anionic or nonionic polymeric particle exhibits selectivity ratio of 2× affinity for at least four perfume raw materials having a Kovats Index on DB-5 of between about 1000 and 1400 than for at least four perfume raw materials having a Kovats Index on DB-5 of greater than about 1600 as measured by the Perfume Deposition & Delivery Test Protocol I described herein.

In still yet another embodiment, the monomers of the polymeric particle may be selected such that the resulting anionic or nonionic polymeric particle exhibits selectivity ratio of 3× affinity for at least four perfume raw materials having a Kovats Index on DB-5 of between about 1000 and 1400 than for at least four perfume raw materials having a Kovats Index on DB-5 of greater than about 1600 as measured by the Perfume Deposition & Delivery Test Protocol I described herein.

In still another embodiment, the monomers of the polymeric particle may be selected such that the resulting anionic or nonionic polymeric particle exhibits selectivity ratio of 3× affinity for a perfume raw material having a Kovats Index on DB-5 of between about 1000 and 1500 than other perfume raw materials having a Kovats Index on DB-5 of greater than about 1700 as measured by the Perfume Deposition & Delivery Test Protocol I and/or the Polymeric Particle Affinity Test Protocol II described herein.

In even another embodiment, the monomers of the polymeric particle may be selected such that the resulting anionic or nonionic polymeric particle exhibits selectivity ratio of 3× affinity for a perfume raw material having a Kovats Index on DB-5 of between about 1000 and 1400 than other perfume raw materials having a Kovats Index on DB-5 of greater than about 1700 as measured by the Perfume Deposition & Delivery Test Protocol I and/or II described herein.

In still yet another embodiment, the monomers of the polymeric particle may be selected such that the resulting anionic or nonionic polymeric particle exhibits selectivity ratio of 5× affinity for at least four perfume raw materials having a Kovats Index on DB-5 of between about 1000 and 1400 than for at least four perfume raw materials having a Kovats Index on DB-5 of greater than about 1600 as measured by the Perfume Deposition & Delivery Test Protocol I described herein.

In still another embodiment, the monomers of the polymeric particle may be selected such that the resulting anionic or nonionic polymeric particle exhibits selectivity ratio of 5× affinity for a perfume raw material having a Kovats Index on DB-5 of between about 1000 and 1500 than other perfume raw materials having a Kovats Index on DB-5 of greater than about 1700 as measured by the Perfume Deposition & Delivery Test Protocol I and/or the Polymeric Particle Affinity Test Protocol II described herein.

In even another embodiment, the monomers of the polymeric particle may be selected such that the resulting anionic or nonionic polymeric particle exhibits selectivity ratio of 5× affinity for a perfume raw material having a Kovats Index on DB-5 of between about 1000 and 1400 than other perfume raw materials having a Kovats Index on DB-5 of greater than about 1700 as measured by the Perfume Deposition & Delivery Test Protocol I and/or II described herein.

In still yet another embodiment, the monomers of the polymeric particle may be selected such that the resulting anionic or nonionic polymeric particle exhibits a 10× affinity for at least four perfume raw materials having a Kovats Index on DB-5 of between about 1000 and 1400 than for at least four perfume raw materials having a Kovats Index on DB-5 of greater than about 1600 as measured by the Perfume Deposition & Delivery Test Protocol I described herein.

In even another embodiment, the monomers of the polymeric particle may be selected such that the resulting anionic or nonionic polymeric particle exhibits a 10× affinity for a perfume raw material having a Kovats Index on DB-5 of between about 1000 and 1400 than other perfume raw materials having a Kovats Index on DB-5 of greater than about 1700 as measured by the Perfume Deposition & Delivery Test Protocol I and/or II described herein.

In still another embodiment, the monomers of the polymeric particle may be selected such that the resulting anionic or nonionic polymeric particle exhibits a 10× affinity for a perfume raw material having a Kovats Index on DB-5 of between about 1000 and 1500 than other perfume raw materials having a Kovats Index on DB-5 of greater than about 1700 as measured by the Perfume Deposition &. Delivery Test Protocol I and/or the Polymeric Particle Affinity Test Protocol II described herein.

The polymeric particle can be derived from about 50% to about 99.9% and/or from about 60% to about 95% by weight of non-cationic monomers, optionally, from about 0.1% to about 50% and/or from about 1% to about 10% by weight of cationic monomers and from about 0% to about 25% and/or from about 1% to about 10% by weight of cross-linking monomers.

The monomers polymerized to form the polymeric particle may be used in a weight ratio of non-cationic monomer:cationic monomer:cross-linking monomer of from about 10:0:0 to about 5:1:1.

In one embodiment, the polymeric particle may have an average particle size of from about 100 nm to about 39 µm.

In another embodiment, the polymeric particle may have an average particle size of from about 3 µm to about 39 µm and/or from about 5 µm to about 20 µm and/or from about 5 µm to about 12 µm.

In yet another embodiment, the polymeric particle may have an average particle size of from about 100 nm to about 1 µm and/or from about 200 nm to about 900 nm and/or from about 700 nm to about 900 nm.

In one embodiment, the polymeric particles have a glass transition temperature, Tg, from about 50° C. to about 150° C., preferably from about 80° C. to about 120° C.

In one embodiment, the polymeric particle may comprise a single polymer after polymerization of the monomers. During polymerization of the monomers, the emulsifier and/or stabilizer may become grafted into the resulting polymeric particle.

In another embodiment, the polymeric particle may comprise two or more polymers. For example, the polymeric particle may comprise a first polymer resulting from the polymerization of the monomers, and a second polymer associated with the first polymer, such as the emulsifier and/or stabilizer (i.e., polyvinylalcohol (PVA)). When the polymeric particle comprises two or more polymers, the concentration of each polymers is preferably from at least about 0.01 weight percent, more preferably at least about 0.1 weight percent, even more preferably at least about 0.25 weight percent, by weight of the personal care composition.

It is desirable that the polymeric particle is stable in aqueous dispersions. Stability of the polymeric particle can be influenced by the average particle size of the resulting polymeric particle and/or the net charge of the resulting polymeric particle.

In one embodiment, the polymeric particle has a net anionic charge, preferably from about −10 mV to about −80 mV and/or from about −30 mV to about −60 mV and/or from about −35 mV to about −55 mV, as measured by a Brookhaven zeta potential analyzer.

In addition, it is desirable that the polymeric particle is stable within product formulations, such as personal care compositions, especially bodywash and hair care compositions in accordance with the present invention.

To aid in the stabilizing the polymeric particle in aqueous dispersions and/or in product formulations, such as personal care compositions, a stabilizer, also known as a colloidal stabilizer may be added to the aqueous dispersion and/or product formulation. It is desirable that the colloidal stabilizer be compatible with other ingredients within the aqueous dispersion and/or product formulation.

The polymeric particle may be water-insoluble. In other words, when added to water, the polymeric particle physically separates from the water (i.e. settles-out, flocculates, floats) within 5 minutes after addition, whereas a material that is "soluble in water" does not physically separate from the water within 5 minutes after addition. Another way of describing water-insoluble materials for purposes of the present invention is the fact that water-insoluble materials are not soluble in distilled (or equivalent) water, at 25° C., at a concentration of greater than about 5% and/or greater than about 3% and/or greater than about 1% by weight (calculated on a water plus polymeric particle weight basis).

The polymeric particle may have a molecular weight of from about 1,000 to about 2,000,000 preferably from about 5,000 to about 1,000,000, more preferably from about 10,000 to about 750,000, more preferably from about 20,000 to about 500,000 daltons. The molecular weight of the polymeric particle can be determined via conventional gel permeation chromatography or any other suitable procedure known to those of ordinary skill in the art.

In one embodiment, the perfume polymeric particle comprises a perfume which comprises greater than 50% by weight of the perfume of perfume raw materials having a molecular weight of less than about 200, a boiling point of less than about 250° C. and a ClogP of less than about 3 and/or a Kovats Index value of less than about 1700.

Even though the polymeric particle of the present invention is an anionic or nonionic polymeric particle, monomers having cationic charges and/or zwitterionic charges can be used with the anionic or nonionic monomer(s) to form the anionic or nonionic polymeric particle.

A nonlimiting example of a suitable anionic polymeric particle is commercially available under the tradename Allianz OPT from Rohm & Haas. The INCI name for Allianz OPT is Acrylates/C12-22 Alkyl Methacrylate Copolymer.

An additional feature of the present invention that the polymeric particle and the perfume raw material are added separately to the personal care composition. For purposes of this invention, in one embodiment the polymeric particle and perfume raw material are separately added to the system-forming matrix if the entire amount of these components is combined with the matrix as discrete components. In particular, there must be essentially no chemical interaction between these two materials before they are combined with the matrix. Thus the polymeric particle and the perfume raw material may be added to the matrix at separate times and/or from separate containers and/or from separate holding or delivery means. The polymeric particle and the perfume raw materials may even be mixed together prior to combination with the system-forming matrix so long as substantially no chemical interaction occurs between these materials prior to their contact with the system-forming matrix.

Non-Cationic Monomer

The non-cationic monomer may be a hydrophobic group-containing monomer. The hydrophobic group may be selected from the group consisting of non-hydroxyl groups, non-cationic groups, non-anionic groups, non-carbonyl groups, and/or non-H-bonding groups, more preferably selected from the group consisting of alkyls, cycloalkyls, aryls, alkaryls, aralkyls and mixtures thereof. The non-cationic monomer may be a hydroxyl-containing monomer. The non-cationic monomer may be an anionic group-containing monomer.

Nonlimiting examples of suitable non-cationic monomers include, but are not limited to, methyl methacrylate, methyl acrylate, ethyl acrylate, n-propyl acrylate, iso-propylacrylate, n-propyl methacrylate, ethyl methacrylate, iso-propylmethacrylate, n-butyl acrylate, isobutyl acrylate, isobutyl methacrylate, n-butyl methacrylate, methacrylic acid, acrylic acid, acrylamide, methacrylamide, styrene, α-methyl styrene, benzyl acrylate, ethylhexylacrylate, hydroxyethylacrylate, hydroxypropylacrylate, hydroxyethylmethacrylate, hydroxypropylmethacrylate, hydroxybutylacrylate, hydroxybutylmethacrylate, PEG acrylate, vinyl ethers, vinyl ketones, vinyl acetate, vinyl phenols, acylamido-2-methyl-propanesulfonic acid, vinlysulfonate, vinylpropionate, methylallylsulfonic acid, and N-vinylformamide.

Cationic Monomer The cationic monomer of the present invention comprises a cationic unit. For the purposes of the present invention the term "cationic unit" is defined as a moiety which when incorporated into the structure of the polymeric particle of the present invention, is capable of maintaining a cationic charge within the pH range of from about 2 to about 8. The cationic unit is not required to be protonated at every pH value within the range of about 2 to about 8. Nonlimiting examples of units which comprise a cationic moiety include the cationic units having the formula:

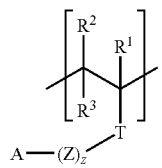
[I]

wherein each of $R^1$, $R^2$ and $R^3$ are independently selected from the group consisting of hydrogen, $C_1$ to $C_6$ alkyl, and mixtures thereof, preferably hydrogen, $C_1$ to $C_3$ alkyl, more preferably, hydrogen or methyl. T is selected from the group consisting of substituted or unsubstituted, saturated or unsaturated, linear or branched radicals selected from the group consisting of alkyl, cycloalkyl, aryl, alkaryl, aralkyl, heterocyclic ring, silyl, nitro, halo, cyano, sulfonato, alkoxy, keto, ester, ether, carbonyl, amido, amino, glycidyl, carbanato, carbamate, carboxylic, and carboalkoxy radicals and mixtures thereof. Z is selected from the group consisting of: —($CH_2$)—, ($CH_2$—CH═CH)—, —($CH_2$—CHOH)—, ($CH_2$—$CHNR^4$)—, —($CH_2$—$CHR^5$—O)— and mixtures thereof, preferably —($CH_2$)—. $R^4$ and $R^5$ are selected from the group consisting of hydrogen, $C_1$ to $C_6$ alkyl and mixtures thereof, preferably hydrogen, methyl, ethyl and mixtures thereof; z is an integer selected from about 0 to about 12, preferably about 2 to about 10, more preferably about 2 to about 6. A is $NR^6R^7$ or $NR^6R^7R^8$, wherein each of $R^6$, $R^7$ and $R^8$, when present, are independently selected from the group consisting of H, $C_1$-$C_8$ linear or branched alkyl, alkyleneoxy having the formula:

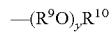
—($R^9$O)$_y R^{10}$ wherein $R^9$ is $C_2$-$C_4$ linear or branched alkylene, and mixtures thereof; $R^{10}$ is hydrogen, $C_1$-$C_4$ alkyl, and mixtures thereof, y is from 1 to about 10. Preferably $R^6$, $R^7$ and $R^8$, when present, are independently, hydrogen, $C_1$ to $C_4$ alkyl. Alternatively, $NR^6R^7$ or $NR^6R^7R^8$ can form a heterocyclic ring containing from 4 to 7 carbon atoms, optionally containing additional hetero atoms, optionally fused to a benzene ring, and optionally substituted by $C_1$ to $C_8$ hydrocarbyl, and/or acetates. Examples of suitable heterocycles, both substituted and unsubstituted, are indolyl, isoindolinyl imidazolyl, imidazolinyl, piperidinyl pyrazolyl, pyrazolinyl, pyridinyl, piperazinyl, pyrrolidinyl, pyrrolidinyl, guanidino, amidino, quinidinyl, thiazolinyl, morpholine and mixtures thereof, with morpholino and piperazinyl being preferred.

Nonlimiting examples of suitable cationic monomers for the present invention include, but are not limited to, dimethylamino alkyl acrylates, especially dimethylaminoethyl methacrylate, vinyl pyrrolidones, vinyl imidazoyls, vinyl ethers having dialkyl amino groups, vinyl pyridines, alkyl acrylamides and dialkylamino alkyl acrylamides.

Cross-Linking Monomer

The cross-linking monomer may be present in the polymeric particle of the present invention. Nonlimiting examples of suitable cross-linking monomers include, but are not limited to, diacrylate, dimethacrylate, diethylene glycol diacrylate, divinylbenzene, divinyl ether, ethylene glycol dimethacrylate, pentaerythritol triacrylate, polyallyl sucrose, trivinyl benzene, divinyl toluene, trivinyl toluene, triethylenglycol dimethacrylate, tetraethylenglycol dimethacrylate, allylmethacrylate, diallylmaleate, triallylmaleate and 1,4-butanediol diacrylate, triallylmaleate 1,2-ethanediol diacrylate, 1,3-propanediol diacrylate, 1,6-hexanediol diacrylate.

Emulsifier and/or Colloidal Stabilizer

Suitable emulsifiers and/or colloidal stabilizers for use in the present invention are known in the art. Nonlimiting examples of such emulsifiers and/or colloidal stablizers include, but are not limited to, ricinolyamidopropyltrimethyl-ammoniummetho sulfate, cocopentylethoxymethyl-ammoniummetho sulfate, cocobis(2-hydroxyethyl) methylammonium chloride, cetyltrimethylammonium bromide, cetylpyridinium chloride, glyceryl stearate, stearadamidoethyl diethylamine, ethoxylated oleylamines, ethoxylated fatty amines, ethoxylated quaternised fatty amines, ethoxylated fatty alcohols, sorbitan stearate, polysorbate, stearate, sodium dodecyl sulfate, ammoniumnonoxynol sulfate, dodecyltrimethyl ammonium bromide, sodium lauryl sulfate, sodium laurate, gelatine, polyvinylalcohol, aminomethylated starch, poly(vinylalcohol-co-vinylacetate) copolymers, modified cellulose like carboxymethyl cellulose, methyl cellulose, hydroxyethyl cellulose, polyoxyethylene, polyvinylpyrrolidone, polyoxyethylene-polyoxypropylene-polyoxyethylene copolymers, polyether-modified dimethicones and polyether-alkyl-dimethicones copolymers, cationic silicones and polyimides.

A colloidal stabilizer may be used to maintain particle dispersive stability, particularly of larger sized particles. Suitable colloidal stabilizer include, but are not limited to, propylene oxide-ethylene oxide copolymers or ethyleneoxide-propylenoxide graphted polyethylenimines, polyoxyethylene (X) isooctylphenyl ether where X is an integer from 20 to 80, fatty alcohol ethoxylates, polyethoxylated polyterephthalate block co-polymers polyvinylpyrrolidone polyvinylpyrrolidone and copolymers containing vinylpyrolidone.

Initiators

Suitable initiators for use in the polymerization process of the present invention are known in the art. Examples include, but are not limited to sodium persulfate and azo initiators such as 2,2'-azobis(2-methylpropionamide)dihydrochloride, 2,2'-azobis(2-amidinopropane)dihydrochloride, 2,2'-azobis(N,N'-dimethyleneisobutyramidine)dihydrochloride, 2,2'-azobis(2-methylbutyronitrile, 2,2'-azobis(4-methoxy-2,4dimethylvaleronitrile, 2-(Carbamoylazo)-isobutyronitrile.

Personal Care Composition

The perfume polymeric particle of the present invention may be incorporated along with one or more personal care adjunct ingredients to form a personal care composition. The personal care composition of the present invention may be in any suitable form, such as liquids, gels, foams, paste, bars, tablets, powders and granules. The preferred form of the present invention is liquids. The product forms of the personal care compositions may include body wash products, shampoo, hair and/or body conditioners, pet hair shampoos and/or conditioners.

Further, in addition to rinse-off types of applications, such as is the focus of the present invention, leave-on types of applications may incorporate the polymeric particles and/or perfume polymeric particles of the present invention. Preferred may be a product that contains greater than 10% by weight of moisture (water).

Protocol III (Direct Applications):

The same procedure is followed as with indirect application, with the exception, that the aliquot of $TS_0$ is not diluted with water or rinsed. A longevity benefit is confirmed for a particular polymeric particle (PP) when the quantitative amount of any PRM in the headspace from $TS_n$ at any one of the designated times points is greater than the amount of the same PRM in the headspace from $TS_c$ at the corresponding time point. For direct addition application, the polymeric particle can serve to "flatten" the release profile of the perfume raw materials when present in the perfume delivery system. This can result in the initial headspace count of a PRM with PP present to be lower than the headspace count of a PRM with no PP present. At initial or later time points however, the longevity benefit is observed. Preferably, the polymeric particles of the present invention increase the longevity of PRMs having a Kovat Index of less than 1700, and more preferably increase the longevity of PRMs having a Kovat Index of less than 1500 to a greater extent than PRMs have a Kovat Index greater than 1700.

The following table demonstrates the type of results that can be obtained from a Longevity Test with Direct applications. The data confirms a longevity benefit for PRM[1] (at t=6 h, the area count from $TS_n>TS_c$) and PRM[2] (at t=2 and 6 h, the area count from $TS_n>TS_c$) in the presence of polymeric particle (PP).

| HSGC Area Count for Benefit Agent with and without PP | | | | | |
| --- | --- | --- | --- | --- | --- |
| Time | PRM[1] (KI = 1033) | | PRM[2] (KI = 1122) | | PRM[3] (KI = 1770) |
| (h) | $TS_c$ | $TS_n$ | $TS_c$ | $TS_n$ | $TS_c$ | $TS_n$ |
| 2 | 3000 | 2500 | 20 | 1000 | 850 | 700 |
| 6 | 750 | 1500 | ND | 150 | 25 | ND |
| 24 | ND | 50 | ND | ND | ND | ND |

ND = Not detected.

Further, in addition to rinse-off types of applications, such as is the focus of the present invention, leave-on types of applications may incorporate the polymeric particles and/or perfume polymeric particles of the present invention.

Preferred may be a product that contains greater than 10% by weight of moisture (water). The perfume polymeric particle may be present in the personal care composition at any suitable level, typically it is present at a level of at least 0.1%, preferably from about 0.1% to about 20%, more preferably from about 1% to about 10% by weight of the personal care composition. In addition to the perfume polymeric particle, it is desirable to incorporate a separate, water-soluble charged polymeric component. It is further preferred that polymer have a charge density of at least about 0.4 meq/gm and less than about 7 meq/gm.

Additionally, a method of depositing perfume polymeric particles onto human skin, hair or nails comprising the steps of applying the personal care compositions as described herein to the skin, hair and/or nails and rinsing off is also provided.

The present invention may be a rinse-off personal care composition, which effectively deposits perfume having a molecular weight of less than about 200, and/or a boiling point of less than about 250° C. and/or a ClogP of less than about 3, and/or a Kovats Index value of less than about 1700 onto the human skin and/or human and/or pet hair.

The personal care compositions of the present invention may include in addition to a perfume polymeric particle according to the present invention, a cationic and/or anionic polymer, preferably a deposition enhancing polymer, and/or conventional adjunct personal care ingredients.

The term "suitable for application to human skin" as used herein, means that the compositions or components thereof so described are suitable for use in contact with human skin without undue toxicity, incompatibility, instability, allergic response, and the like.

The term "water soluble" as used herein, means that the polymer is soluble in water in the present composition. In general, the polymer should be soluble at 25° C. at a concentration of 0.1% by weight of the water solvent, preferably at 1%, more preferably at 5%, most preferably at 15%.

Personal Care Adjunct Ingredients

Deposition Polymers

The personal care compositions of the present invention may include deposition polymers that may facilitate deposition of the perfume polymeric particles. These deposition polymers may be anionic, cationic, nonionic and/or zwitterionic.

In one embodiment, the personal care composition comprises a cationic deposition polymer in addition to the anionic polymeric particle and/or perfume polymeric particle. It is desirable that the cationic deposition polymer and the anionic polymeric particle and/or perfume polymeric particle are aggregated prior to being added to the personal care composition.

The compositions of the present invention may include a "Cationic Deposition Polymer" (CDP) of sufficiently high cationic charge density to effectively enhance deposition of the solid particle component described herein. Suitable cationic polymers will have cationic charge densities of at least about 0.4 meq/gm, preferably at least about 0.7 meq/gm, more preferably at least about 0.9 meq/gm, but also preferably less than about 7 meq/gm, more preferably less than about 5 meq/gm, at the pH of intended use of the personal care composition, which pH will generally range from about pH 2 to about pH 9, preferably between about pH 4 and about pH 8. The average molecular weight of such suitable cationic polymers will generally be between about 10,000 and 10 million, preferably between about 50,000 and about 5 million, more preferably between about 100,000 and about 3 million. The "cationic charge density" of a polymer, as that term is used herein, refers to the ratio of the number of positive charges on a monomeric unit of which the polymer is comprised to the molecular weight of said monomeric unit. The cationic charge density multiplied by the polymer molecular weight determines the number of positively charged sites on a given polymer chain.

The concentration of the cationic polymer in the personal care composition ranges from about 0.05% to about 3%, preferably from about 0.075% to about 2.0%, more preferably from about 0.1% to about 1.0%, by weight of the personal care composition. The weight ratio of Cationic Deposition Polymer to perfume polymeric particle in the personal care compositions is from about 2:1 to about 1:100, preferably from about 1:1 to about 1:50, more preferably from about 1:1 to about 1:30.

The Cationic Deposition Polymer(s) for use in the personal care composition of the present invention contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal care composition. Any anionic counterions can be used in association with the Cationic Deposition Polymer(s) so long as the polymers preferably remain soluble in water, in the personal care composition, or in a coacervate phase of the personal care composition, and so long as the counterions are physically and chemically compatible with the essential components of the personal care composition or do not otherwise unduly impair product performance, stability or aesthetics. Non limiting examples of such counterions include halides (e.g., chlorine, fluorine, bromine, iodine), sulfate and methylsulfate.

The cationic nitrogen-containing moiety of the Cationic Deposition Polymer is generally present as a substituent on all, or more typically on some, of the monomer units thereof. Thus, the cationic deposition polymers for use in the personal care composition include homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which description is incorporated herein by reference.

Suitable deposition polymers for use in the personal cleaning compositions described herein will preferably have a settling time of less than the settling time of the same compositions without the deposition polymer added, as determined by the flocculation/settling test described below.

Flocculation/Settling Test 4 grams of neat product is placed into a 50 ml conical bottom centrifuge tube (Corning part # 430304 or similar) and diluted with 36 grams of distilled water. The tube is then capped and shaken vigorously until the entire product has been dispersed. This is considered the initial time. The tube is then let stand vertically. For products containing polymeric particles, the system will be opaque due to the suspension of the polymeric particles. To screen polymer systems and particular orders of additions, batches with and without polymer, or made via different addition methods are made and compared in this test. Preferred polymers and orders of addition result in a flocculation of the particles on a rapid time scale, generally on the order of less than 30 minutes, however, any flocculation time less than that of the same composition without polymer or a composition made via a different addition method indicates a suitable deposition polymer, or order of addition. Flocculation can be observed by the formation of clear areas in the diluted samples as the polymeric particles are aggregated and removed from the suspension which will initially be nearly homogeneously opaque. The time taken for this to occur to a noticeable degree is considered the flocculation time.

Suitable cationic deposition polymers for use in the personal care composition may include polysaccharide polymers, such as cationic cellulose derivatives and cationic starch derivatives. Suitable cationic polysaccharide polymers include those, which conform to the formula:

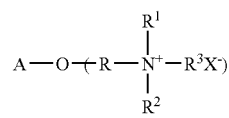

wherein A is an anhydroglucose residual group, such as a starch or cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion, as previously described. The degree of cationic substitution in these polysaccharide polymers is typically from about 0.01-1 cationic groups per anhydroglucose unit.

Preferred cationic cellulose polymers salts of hydroxyethyl cellulose reacted with trimethyl ammonium substituted epoxide, referred to in the industry (CTFA) as Polyquaternium 10 and available from Amerchol Corp. (Edison, N.J., USA) as Polymer JR30M with charge density of 1.25 meq/g and molecular weight of ~900,000, Polymer JR400 with charge density of 1.25 meq/g and molecular weight of ~400,000, and Polymer KG30M with a charge density of 1.9 and a molecular weight of ~1.25 million. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24.

Other suitable cationic polymers include cationic guar gum derivatives, such as guar hydroxypropyltrimonium chloride, a specific examples of which includes Jaguar C17 with a charge density of 0.9 and molecular weight of ~2.2 million commercially available from Rhone-Poulenc Incorporated. Other suitable cationic polymers include quaternary nitrogen-containing cellulose ethers, some examples of which are described in U.S. Pat. No. 3,962,418, which description is incorporated herein by reference herein. Other suitable cationic polymers include copolymers of etherified cellulose, guar and starch, some examples of which are described in U.S. Pat. No. 3,958,581, which description is incorporated herein by reference.

Cleansing Surfactant

The personal care compositions of the present invention may comprise a surfactant suitable for application to the hair or skin. Suitable surfactants for use herein include any known or otherwise effective care surfactant suitable for application to the hair or skin, and which is otherwise compatible with the other essential ingredients in the compositions. Suitable cleansing surfactants include anionic, nonionic, cationic, zwitterionic or amphoteric surfactants, or combinations thereof.

The personal care compositions of the present invention preferably comprise from about 0.1% to about 50%, more preferably from about 4% to about 30%, even more preferably from about 5% to about 25%, by weight of the composition of cleansing surfactant.

Anionic surfactants suitable for use in the personal care compositions include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium or triethanolamine. The alkyl ether sulfates are typically made as condensation products of ethylene oxide and monohydric alcohol's having from about 8 to about 24 carbon atoms. Preferably, R has from about 10 to about 18 carbon atoms in both the alkyl and alkyl ether sulfates. The alcohol's can be derived from fats, e.g., coconut oil or tallow, or can be synthetic. Lauryl alcohol and straight chain alcohol's derived from coconut oil are preferred herein. Such alcohol's are reacted with about 1 to about 10, preferably from about 3 to about 5, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the personal care compositions include are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula $[R^1—SO_3—M]$, wherein $R^1$ is chosen from the group consisting of a straight or branched chain, saturated aliphatic hydrocarbon radical having from about 8 to about 24, preferably about 10 to about 18, carbon atoms; and M is a cation. Preferred examples include the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Additional examples of suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other suitable anionic surfactants of this variety are described in U.S. Pat. No. 2,486,921; U.S. Pat. No. 2,486,922; and U.S. Pat. No. 2,396,278; which descriptions are incorporated herein by reference.

Still other suitable anionic surfactants are the succinamates, examples of which include disodium N-octadecylsulfosuccinamate; diammoniumlauryl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having from about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

Another class of anionic surfactants suitable for use in the personal care compositions of the present invention is the α-alkyloxy alkane sulfonates, which conform to the formula:

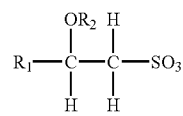

wherein $R_1$ is a straight chain alkyl group having from about 6 to about 20 carbon atoms, $R_2$ is a lower alkyl group having from about 1 to about 3 carbon atoms, preferably 1 carbon atom, and M is a water-soluble cation.

Other suitable surfactants for use in the personal care compositions herein are described in *McCutcheon's, Emulsifiers and Detergents*, 1989 *Annual*, published by M. C. Publishing Co., and in U.S. Pat. No. 3,929,678, which descriptions are incorporated herein by reference.

Preferred anionic surfactants for use in the personal care compositions herein include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Amphoteric surfactants suitable for use in the personal care compositions herein include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Non-limiting examples of such surfactants include sodium 3-dodecyl-aminopropionate, sodium 3-dodecylaminopropane sulfonate, sodium lauryl sarcosinate, N-alkyltaurines such as those prepared by reacting dodecylamine with sodium isethionate according to the teaching of U.S. Pat. No. 2,658,072, N-higher alkyl aspartic acids such as those prepared in accordance with the teaching of U.S. Pat. No. 2,438,091, and the products described in U.S. Pat. No. 2,528,378, which teachings and descriptions are incorporated herein by reference.

Other suitable amphoteric surfactants include the alkali, alkaline earth, ammonium and trialkanolammonium salts of cocoamphoacetate, cocoamphodiacetate, cocoamphopropionate, cocoamphodipropionate, amphoacetates such as lauroamphoacetate or cocoamphoacetate and mixtures thereof.

Also suitable are soaps—mono and divalent salts of fatty acids.

Cationic surfactants can also be used in the personal care compositions herein, but are generally less preferred, and preferably represent less than about 5% by weight of the compositions.

Suitable nonionic surfactants for use in the personal care compositions herein include condensation products of alkylene oxide groups with an organic hydrophobic compound, which may be aliphatic or alkyl aromatic in nature. Preferred classes of nonionic surfactants include:

1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the ethylene oxide being present in amounts equal to from about 10 to about 60 moles of ethylene oxide per mole of alkyl phenol;
2) nonionic surfactants derived from the condensation of ethylene oxide with the product resulting from the reaction of propylene oxide and ethylene diamine products;
3) condensation products of aliphatic alcohol's having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;
4) long chain tertiary amine oxides corresponding to the following general formula:

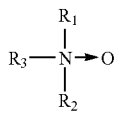

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals;

5) long chain tertiary phosphine oxides corresponding to the following general formula:

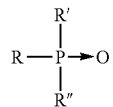

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms;

6) long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety;

7) alkyl polysaccharide (APS) surfactants such as the alkyl polyglycosides, as described in U.S. Pat. No. 4,565,647, which have a hydrophobic group with about 6 to about 30 carbon atoms and polysaccharide (e.g., polyglycoside) as the hydrophilic group, and optionally have a polyalkylene-oxide group joining the hydrophobic and hydrophilic moieties, wherein the alkyl group (i.e., the hydrophobic moiety) can be saturated or unsaturated, branched or unbranched, and unsubstituted or substituted (e.g., with hydroxy or cyclic rings); and 8) polyethylene glycol (PEG) glyceryl fatty esters, such as those of the formula $R(O)OCH_2CH(OH)CH_2(OCH_2CH_2)_nOH$ wherein n is from about 5 to about 200, preferably from about 20 to about 100, and R is an aliphatic hydrocarbyl having from about 8 to about 20 carbon atoms.

Zwitterionic surfactants suitable for use in the personal care compositions herein include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. These zwitterionic surfactants include those represented by the formula:

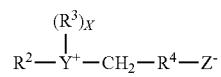

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use in the personal care compositions herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alphacarboxyethyl betaine. The sulfobetaines may be represented by cocodimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Conventional Personal Care Adjunct Ingredients

The personal care compositions of the present invention may further comprise other personal care adjunct ingredients that may modify the physical, chemical, cosmetic or aesthetic characteristics of the compositions or serve as additional "active" components when deposited on the skin. The compositions may also further comprise adjunct inert ingredients. Many such adjunct ingredients are known for use in personal care compositions, and may also be used in the topical compositions herein, provided that such adjunct materials are compatible with the essential materials described herein, or do not otherwise unduly impair product performance.

Such adjunct ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Non limiting examples of such adjunct ingredients include preservatives (e.g., propyl paraben), deodorants, antimicrobials, fragrances, deodorant perfumes, coloring agents or dyes, thickeners, sensates, sunscreens, surfactants or emulsifiers, gellants or other suspending agents, pH modifiers, co-solvents or other additional solvents, emollients, pharmaceutical actives, vitamins, and combinations thereof.

The personal care compositions of the present invention may optionally contain one or more of such adjunct ingredients. Examples of these ingredient classes include: enzymes, abrasives, skin exfoliating agents, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, additional antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin-conditioning agents (humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, including agents for preventing, retarding, arresting, and/or reversing skin wrinkles (e.g., alpha-hydroxy acids such as lactic acid and glycolic acid and beta-hydroxy acids such as salicylic acid), thickeners, hydrocolloids, particular zeolites, and vitamins and derivatives thereof (e.g. tocopherol, tocopherol acetate, beta carotene, retinoic acid, retinol, retinoids, retinyl palmitate, niacin, niacinamide, and the like). The personal care compositions of the present invention may include carrier components such as are known in the art. Such carriers can include one or more compatible liquid or solid filler diluents or vehicles which are suitable for application to skin or hair.

The personal care compositions of the present invention may optionally contain one or more of such adjunct ingredients. Preferred personal care compositions optionally contain a safe and effective amount of an therapeutic benefit component comprising a therapeutic benefit agent selected from the group consisting of vitamin compounds, conditioning agents, skin treating agents, anti-acne actives, anti-wrinkle actives, anti-skin atrophy actives, anti-inflammatory actives, topical anesthetics, artificial tanning actives and accelerators, antimicrobial actives, anti-fungal actives, sunscreen actives, antioxidants, skin exfoliating agents, and combinations thereof. As used herein, "a safe and effective amount" means an amount of a compound or component sufficient to significantly induce a positive effect or benefit, but low enough to avoid serious side effects, (e.g., undue toxicity or allergic reaction), i.e., to provide a reasonable benefit to risk ratio, within the scope of sound medical judgment.

The personal care compositions of the present invention may further comprise a stabilizing agent at concentrations effective for stabilizing the particle, or other water-insoluble material, in dispersed form in the personal care compositions or for modifying the viscosity of the composition. Such concentrations range from about 0.1% to about 10%, preferably from about 0.3% to about 5.0%, by weight of the personal care compositions.

Stabilizing agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Polyalkylene glycols having a molecular weight of more than about 1000 are useful herein. Useful are those having the following general formula:

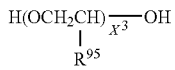

wherein $R^{95}$ is selected from the group consisting of H, methyl, and mixtures thereof. When $R^{95}$ is H, these materials are polymers of ethylene oxide, which are also known as polyethylene oxides, polyoxyethylenes, and polyethylene glycols. When $R^{95}$ is methyl, these materials are polymers of propylene oxide, which are also known as polypropylene oxides, polyoxypropylenes, and polypropylene glycols. When $R^{95}$ is methyl, it is also understood that various positional isomers of the resulting polymers can exist. In the above structure, x3 has an average value of from about 1500 to about 25,000, preferably from about 2500 to about 20,000, and more preferably from about 3500 to about 15,000. Other useful polymers include the polypropylene glycols and mixed polyethylene-polypropylene glycols, or polyoxyethylene-polyoxypropylene copolymer polymers. Polyethylene glycol polymers useful herein are PEG-2M wherein $R^{95}$ equals H and x3 has an average value of about 2,000 (PEG-2M is also known as Polyox WSR® N-10, which is available from Union Carbide and as PEG-2,000); PEG-5M wherein $R^{95}$ equals H and x3 has an average value of about 5,000 (PEG-5M is also known as Polyox WSR® N-35 and Polyox WSR® N-80, both available from Union Carbide and as PEG-5,000 and Polyethylene Glycol 300,000); PEG-7M wherein $R^{95}$ equals H and x3 has an average value of about 7,000 (PEG-7M is also known as Polyox WSR® N-750 available from Union Carbide); PEG-9M wherein $R^{95}$ equals H and x3 has an average value of about 9,000 (PEG 9—M is also known as Polyox WSR® N-3333 available from Union Carbide); and PEG-14 M wherein $R^{95}$ equals H and x3 has an average value of about 14,000 (PEG-14M is also known as Polyox WSR® N-3000 available from Union Carbide).

Commercially available viscosity modifiers highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol.

Other adjunct stabilizing agents include crystalline stabilizing agents which can be categorized as acyl derivatives, long chain amine oxides, and mixtures thereof. These stabilizing agents are described in U.S. Pat. No. 4,741,855, which description is incorporated herein by reference. These preferred stabilizing agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable stabilizing agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin R available from Rheox, Inc. Long chain acyl derivatives, ethylene glycol esters of long chain carboxylic acids, long chain amine oxides, and alkanol amides of long chain carboxylic acids in addition to the preferred materials listed above may be used as stabilizing agents.

Other long chain acyl derivatives suitable for use as stabilizing agents include N,N-dihydrocarbyl amido benzoic acid and soluble salts thereof (e.g., Na, K), particularly N,N-di(hydrogenated) C.sub.16, C.sub.18 and tallow amido benzoic acid species of this family, which are commercially available from Stepan Company (Northfield, Ill., USA).

Examples of suitable long chain amine oxides for use as stabilizing agents include alkyl (C.sub.16-C.sub.22) dimethyl amine oxides, e.g., stearyl dimethyl amine oxide.

Other suitable stabilizing agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable stabilizing agents include di(hydrogenated tallow)phthalic acid amide, and crosslinked maleic anhydride-methyl vinyl ether copolymer.

Other suitable stabilizing agents include crystalline, hydroxyl-containing stabilizers. These stabilizers can be hydroxyl-containing fatty acids, fatty esters or fatty soap water-insoluble wax-like substances or the like. If present, crystalline, hydroxyl-containing stabilizers may comprise from about 0.5% to about 10%, preferably from about 0.75% to about 8%, more preferably from about 1.25% to about 5% by weight of the compositions herein. The said stabilizer is insoluble in water under ambient to near ambient conditions.

Suitable crystalline, hydroxyl-containing stabilizers include:

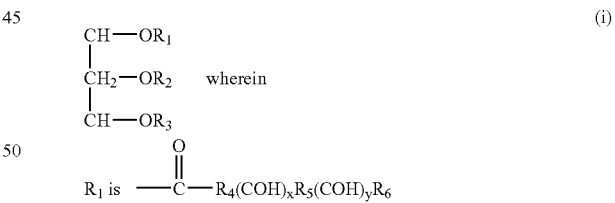

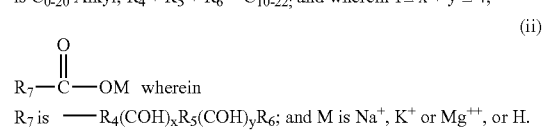

Some preferred hydroxyl-containing stabilizers include 12-hydroxystearic acid, 9,10-dihydroxystearic acid, tri-9,10-dihydroxystearin and tri-12-hydroxystearin (hydrogenated castor oil is mostly tri-12-hydroxystearin). Tri-12-hydroxystearin is most preferred for use in the compositions herein.

The adjunct ingredients as described herein shall specifically exclude, however, any essential ingredient or material as otherwise described or defined herein. However, it should be understood that compositions according to the present invention may contain additional polymers as adjunct ingredients separate from the deposition polymer that may be premixed with the perfume polymeric particles and/or polymeric particles.

Method of Use

The personal care compositions of the present invention are used in a conventional manner for care hair and/or skin and providing enhanced deposition of solid particles and other benefits of the present invention. An effective amount of the composition for care the hair or skin is applied to the hair or skin that has preferably been wetted with water, and then rinsed off. Such effective amounts generally range from about 1 g to about 50 g, preferably from about 1 g to about 20 g.

This method for caring/cleansing the hair and skin comprises the steps of:
a) wetting the hair and/or skin with water;
b) applying an effective amount of the personal care composition to the hair and/or skin; and
c) rinsing the composition from the hair and/or skin using water.

These steps can be repeated as many times as desired to achieve the desired care and particle deposition benefits.

EXAMPLES

The following examples further describe and demonstrate the preferred embodiments within the scope of the present invention. The examples are given solely for the purpose of illustration, and are not to be construed as limitations of the present invention since many variations thereof are possible without departing from its scope.

Shampoo and Bodywash Compositions

| | Component | 1 | 2 | 3 |
|---|---|---|---|---|
| 1 | Sodium lauryl ether 2EO sulfate | 7 | 7 | 7 |
| 2 | Cocoamidopropyl Betaine | 2 | 2 | 2 |
| 3 | Sodium Lauroyl Sarcosinate | 2 | 2 | 3 |
| 4 | Sodium Lauryl Sulfate | 3 | 3 | 3 |
| 5 | Polymeric Particle-Allianz OPT (ISP and Rohm and Haas) | — | 5 | 5 |
| 6 | Glydant | 0.21 | 0.21 | 0.21 |
| 7 | Ucare KG-30M | 0.35 | 0.35 | — |
| 8 | Nhance 3169 | — | — | 0.25 |
| 9 | Water | QS | QS | QS |
| 10 | Sodium Sulfate | 1 | 1 | 1 |
| 11 | Citric Acid | Adjust pH | Adjust pH | Adjust pH |
| 12 | EDTA | 0.15 | 0.15 | 0.15 |
| 13 | Trihydroxystearin | 1.5 | 1.5 | 1.5 |
| 14 | Lauric Acid | 0.5 | 0.5 | 0.5 |
| 15 | Fragrance (appropriate composition) | 2 | 2 | 2 |

Method of manufacture for above examples.

Mix the surfactants (1-4), EDTA (12), Trihydroxystearin (13), and Lauric Acid (14) in a container and heat to 190° F. and allowed to cool. When the temperature drops below 140° F., mix glydant (6) in.

In a separate container, completely hydrate the cationic deposition polymer (7, 8) in the water (9) until the solution is clear and viscous. Then, add the Allianz OPT (5) to the mixture and mix until homogeneous. Then, add Fragrance (15) to the container and mix. Following this step, add the pre-made surfactant mixture from the first step to the container and mix the entire batch well until smooth. Then adjust the pH to 6.3 and use Sodium Sulfate to adjust the viscosity to between 7000 cps and 10,000 cps.

Comparative Method of Manufacture

Prepare the surfactant mixture in the manner described above. Hydrate the cationic deposition polymer also as previously described. Add the surfactant to the hydrated deposition polymer, follow with the fragrance and allow to mix well. Then add the Allianz OPT to the mixture. Then adjust the pH to 6.3 and use Sodium Sulfate to adjust the viscosity to between 7000 cps and 10,000 cps.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
a) a personal care adjunct ingredient; and
b) a water insoluble perfume polymeric particle having an average particle size of from about 100 nm to about 39 µm; said water insoluble perfume polymeric particle comprising:
i) a anionic polymer and
ii) a perfume comprising one or more perfume raw materials having one or more of the following characteristics;
a) a number molecular weight of less than about 200;
b) a boiling point of less than about 250° C;
c) a ClogP of less than about 3; and
d) a Kovats Index value of less than about 1700;
wherein a Response Factor (RF) of the perfume polymeric material is at least about 1.6;
wherein said personal care composition further comprises a cationic deposition polymer aggregated with said perfume polymeric particle.

2. The personal care composition according to claim 1, further comprising at least about 0.1 weight percent of one or more perfume raw material.

3. The personal care composition according to claim 2, wherein at least 25 weight percent of said perfume raw materials have a Kovats Index value of less than about 1700.

4. The personal care composition according to claim 1 wherein said perfume polymeric polymer further comprising a cationic monomer.

5. The personal care composition according to claim 4 wherein said cationic monomer having the formula:

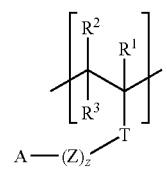

[I]

wherein each of $R^1$, $R^2$ and $R^3$ are independently selected from the group consisting of hydrogen, $C_1$ to $C_6$ alkyl, and mixtures thereof; T is selected from the group consisting of substituted or unsubstituted, saturated or unsaturated, linear or branched radicals selected from the group consisting of alkyl, cycloalkyl, aryl, alkaryl, aralkyl, heterocyclic ring, silyl, nitro, halo, cyano, sulfonato, alkoxy, keto, ester, ether, carbonyl, amido, amino, glycidyl, carbanato, carbamate, carboxylic, and carboalkoxy radicals and mixtures thereof; Z is selected from the group consisting of: —$(CH_2)$—, $(CH_2$—$CH=CH)$—, —$(CH_2$—$CHOH)$—, $(CH_2$—$CHNR^4)$—, —$(CH_2$—$CHR^5$—$O)$— and mixtures thereof; z is an integer selected from about 0 to about 12; A is selected from the group consisting of $NR^6R^7$, $NR^6R^7R^8$ and mixtures thereof;

wherein each of $R^6$, $R^7$ and $R^8$, when present, are independently selected from the group consisting of H, $C_1$-$C_8$ linear, branched alkyl, alkyleneoxy having the formula:

—$(R^9O)_y R^{10}$ and mixtures thereof:

wherein $R^9$ is selected from the group consisting of $C_2$-$C_4$ linear, branched alkylene, carbonyl alkyl, and mixtures thereof; $R^{10}$ is selected from the group consisting of hydrogen, $C_1$-$C_4$ alkyl carbonyl alkyl, and mixtures thereof: y is from 1 to about 10.

6. The personal care composition according to claim 1 wherein the cationic deposition polymer is selected from cationic deposition polymers with flocculation time of less than 30 minutes as described in a Flocculation/Settling Test.

7. The personal care composition according to claim 1 wherein perfume polymeric particles further comprises non-cationic monomer comprising a hydrophobic group selected from the group consisting of alkyls, cycloalkys, aryls, alkaryls, aralkyls and mixtures thereof.

8. The personal care composition according to claim 7 wherein the non-cationic monomer is selected from the group consisting of: methyl methacrylate, methyl acrylate, ethyl acrylate, n-propyl acrylate, iso-propylacrylate, n-propyl methacrylate, ethyl methacrylate, iso-propylmethacrylate, n-butyl acrylate, isobutyl acrylate, isobutyl methacrylate, n-butyl methacrylate, methacrylic acid, acrylic acid, acrylamide, methacrylamide, styrene, α-methyl styrene, benzyl acrylate, ethylhexylacrylate, hydroxyethylacrylate, hydroxypropylacrylate, hydroxyethylmethacrylate, hydroxypropylmethacrylate, hydroxybutylacrylate, hydroxybutylmethacrylate, PEG acrylate, acylamido-2-methylpropanesulfonic acid, vinlysulfonate, vinylpropionate, methylallylsulfonic acid, N-vinylformamide and N-vinylpyrrolidone and mixtures thereof.

9. The personal care composition according to claim 1 wherein greater amounts of said perfume raw material is deposited onto a substrate and released from a substrate when the perfume raw material is associated with said polymer in the form of the perfume polymeric particle as measured by the Perfume Deposition & Delivery Test Protocol I.

10. The personal care composition of claim 1, wherein one or more Low Kovats Index perfume raw materials, each having a Kovats Index value of from about 1000 to about 1400, and collectively provide a first Average Response Factor ($ARF_{LKI}$); and one or more High Kovats Index perfume raw materials, each having a Kovats Index value of greater than about 1700, and collectively provide a second Average Response Factor ($ARF_{HKI}$);

wherein the perfume polymeric particle has a selectivity ratio Of $ARF_{LKI}/ARF_{HKI}$ of at least about 1.2.

11. The personal care composition of claim 10 wherein Longevity Test I value provides an $ARF_{LKI}$ greater than or equal to 1.6 times the value of $ARF_{HKI}$.

12. The personal care composition of claim 10 wherein Longevity Test II value provides an $ARF_{LKI}$ greater than or equal to 1.6 times the value of $ARF_{LKI}$.

13. A personal care composition comprising:
a) a personal care adjunct ingredient; and
b) a water insoluble perfume polymeric particle having an average particle size of from about 100 nm to about 39 μm; said water insoluble perfume polymeric particle comprising:
i) a anioinic polymer which exhibits a greater affinity for a perfume raw material having a Kovats Index value of less than about 1700, than other perfume raw materials as measured by the Perfume Deposition & Delivery Test Protocol I and/or the Polymeric Particle Affinity Test Protocol II wherein the Longevity Test II value provides a $ARF_{LKI}$ greater than or equal to 1.2 times the value of $ARF_{HKI}$;

wherein said personal care composition further comprises a cationic deposition polymer aggregated with said perfume polymeric particle.

14. The personal care composition according to claim 13 wherein said polymer exhibits at least a 1.6 times the affinity for a perfume raw material having a Kovats Index on DB-5 of between about 1000 to about 1500 than other perfume raw materials having a Kovats Index on DB-5 of greater than about 1700 as measured by the Perfume Deposition & Delivery Test Protocol I and the Polymeric Particle Affinity Test Protocol II.

15. A method for making a personal care composition, which exhibits enhanced fragrance intensity on skin and hair over time, comprising
a. forming a preformed water insoluble polymeric particle having an average particle size of from about 100 nm to about 39 μm; said water insoluble polymeric particle comprising a anionic polymer which exhibits a greater affinity for a perfume raw material having one or more of the following characteristics;
i) a number molecular weight of less than about 200;
ii) a boiling point of less than about 250° C.;
iii) a ClogP of less than about 3;
iv) a Kovats Index value of less than about 1700, than other perfume raw materials as measured by the Perfume Deposition & Delivery Test Protocol I and/or the Polymeric Particle Affinity Test Protocol II;
b. forming a perfume polymeric particle by mixing the preformed polymeric particles with a perfume comprising a perfume raw material having one or more of the following characteristics;
i) a molecular weight of less than about 200;
ii) a boiling point of less than about 250° C.;
iii) a ClogP of less than about 3; and
iv) a Kovats Index value of less than about 1700 to; and
c. contacting the perfume polymeric particle with a personal care adjunct ingredient to form the personal care composition ;wherein said personal care composition further comprises a cationic deposition polymer aggregated with said perfume polymeric particle.

16. A method for treating skin and hair of human and pet subject in need of treatment comprising:
a) contacting the subject with a water insoluble perfume polymeric particle having an average particle size of from about 100 nm to about 39 μm; said water insoluble perfume polymeric particle comprising:

i) a anionic polymer, wherein said anionic polymer further comprises and a perfume comprising one or more perfume raw materials having one or more of the following characteristics:
  a) a number molecular weight of less than about 200;
  b) a boiling point of less than about 250° C.;
  c) a ClogP of less than about 3;
  d) a Kovats Index value of less than about 1700;
  wherein a cationic deposition polymer aggregated with said perfume polymeric particle; and
b) rinsing off the personal care composition, such that the subject's skin and hair is treated.

17. A method for treating human and animal subject's hair and skin comprising:
  a) contacting the subject's skin and hair with a water insoluble perfume polymeric particle having an average particle size of from about 100 nm to about 39 μm; said water insoluble perfume particle comprising:
    i) an anionic polymer; and a perfume comprising one or more perfume raw materials having one or more of the following characteristics;
      a) a number molecular weight of less than about 200;
      b) a boiling point of less than about 250° C.;
      c) a ClogP of less than about 3;
      d) a Kovats Index value of less than about 1700;
    wherein a cationic deposition polymer aggregated with said perfume polymeric particle; and
  a) leaving on the personal care composition, such that subject's skin and hair is treated.

18. A personal care composition comprising two or more different water insoluble polymeric particles having an average particle size of from about 100 nm to about 39 μm and a perfume comprising;
  a) a perfume raw material having a one or more of the following characteristics;
    i) a number molecular weight of less than about 200;
    ii) a boiling point of less than about 250° C.;
    iii) a ClogP of less than about 3:
    iv) a Kovats Index value of less than about 1700; and
  b) a personal care adjunct ingredient;
  wherein the Longevity Test II value provides a $ARF_{LKI}$ greater than or equal to 1 .2times the value of $ARF_{HKI}$
  wherein said personal care composition further comprises a cationic deposition polymer aggregated with said perfume polymeric particle.

19. The personal care composition according to claim 18, further comprising at least about .01 weight percent of said polymeric particle.

* * * * *